(12) United States Patent
Huber et al.

(10) Patent No.: US 8,803,020 B2
(45) Date of Patent: Aug. 12, 2014

(54) METHOD AND AN APPARATUS FOR DETECTING LEADED PIECES OF GLASS

(75) Inventors: Reinhold Huber, Fuerstenfeld (AT); Karl Leitner, Anger (AT)

(73) Assignee: Binder + Co AG, Gleisdorf (AT)

( * ) Notice: Subject to any disclaimer, the term of this patent is extended or adjusted under 35 U.S.C. 154(b) by 69 days.

(21) Appl. No.: 13/390,970

(22) PCT Filed: Feb. 26, 2010

(86) PCT No.: PCT/EP2010/052457
§ 371 (c)(1),
(2), (4) Date: Feb. 17, 2012

(87) PCT Pub. No.: WO2011/020628
PCT Pub. Date: Feb. 24, 2011

(65) Prior Publication Data
US 2012/0145607 A1    Jun. 14, 2012

(30) Foreign Application Priority Data
Aug. 19, 2009 (AT) ................................ GM520/2009

(51) Int. Cl.
B07C 5/00 (2006.01)
(52) U.S. Cl.
USPC ............................ 209/524; 209/577; 209/578
(58) Field of Classification Search
CPC .......... G01N 2033/0078; G01N 21/64; G01N 33/386; B07C 5/3427
USPC ........... 271/524, 577, 578; 209/524, 577, 578
See application file for complete search history.

(56) References Cited

U.S. PATENT DOCUMENTS

| | | | | |
|---|---|---|---|---|
| 4,765,484 A | * | 8/1988 | Klumparendt | 209/577 |
| 5,314,071 A | * | 5/1994 | Christian et al. | 209/4 |
| 5,663,997 A | * | 9/1997 | Willis et al. | 378/45 |
| 7,355,140 B1 | * | 4/2008 | Afsari | 209/580 |
| 7,450,684 B2 | * | 11/2008 | Tani et al. | 378/45 |
| 7,550,746 B2 | | 6/2009 | Tokhtuev et al. | |
| 7,659,486 B2 | * | 2/2010 | Valerio | 209/581 |
| 7,757,863 B2 | * | 7/2010 | Bohlig et al. | 209/37 |

(Continued)

FOREIGN PATENT DOCUMENTS

| | | |
|---|---|---|
| DE | 43 39 822 | 5/1995 |
| EP | 0 263 015 | 4/1988 |
| EP | 1 752 228 | 2/2007 |
| WO | WO 2004/063729 | 7/2004 |

OTHER PUBLICATIONS

International Search Report of PCT/EP2010/052457, date of mailing Jun. 23, 2010.

*Primary Examiner* — Jeremy R Severson
(74) *Attorney, Agent, or Firm* — Collard & Roe, P.C.

(57) ABSTRACT

The invention relates to a method and an apparatus for detecting leaded pieces of glass in a single-layer material flow of objects composed predominantly of waste glass, with the objects being irradiated with substantially monochromatic UV light (3) and the fluorescent light resulting therefrom being detected.
It is provided therein that
the object is additionally irradiated with visible or infrared light (4);
the transmission light of the visible or infrared light (4) is detected after the passage through the object;
and an object is defined as containing lead if both the fluorescent light for at least one predetermined wavelength range corresponding to the fluorescence of leaded glasses is present in a predetermined intensity range and also transmission light in a predetermined intensity range with an intensity of larger zero.

18 Claims, 2 Drawing Sheets

(56) References Cited

U.S. PATENT DOCUMENTS

| | | | |
|---|---|---|---|
| 7,918,343 B2 * | 4/2011 | Bohlig et al. | 209/12.1 |
| 8,030,589 B2 | 10/2011 | Huber et al. | |
| 8,127,933 B2 * | 3/2012 | Bohlig et al. | 209/555 |
| 2006/0087826 A1 * | 4/2006 | Anderson, Jr. | 362/23 |
| 2007/0029233 A1 * | 2/2007 | Reinhold et al. | 209/578 |
| 2007/0187305 A1 * | 8/2007 | Valerio | 209/578 |

* cited by examiner

METHOD AND AN APPARATUS FOR DETECTING LEADED PIECES OF GLASS

CROSS REFERENCE TO RELATED APPLICATIONS

This application is the National Stage of PCT/EP2010/052457 filed on Feb. 26, 2010, which claims priority under 35 U.S.C. §119 of Austrian Application No. GM 520/2009 filed on Aug. 19, 2009, the disclosure of which is incorporated by references. The international application under PCT article 21(2) was not published in English.

BACKGROUND OF THE INVENTION

The present invention relates to a method for detecting leaded pieces of glass in a single-layer material flow of objects made predominantly of waste glass, with the objects being irradiated with substantially monochromatic UV-light and the fluorescent light resulting therefrom being detected, and to a respective apparatus.

DESCRIPTION OF THE PRIOR ART

Waste glass usually contains normal glass shards, but can also contain leaded pieces of glass (lead glass) and low-transparent or non-transparent impurities such as ceramics, stones and/or china.

The recycling of waste glass, which also includes glass cullet and an organized collecting and separating process, has already been practiced for a considerable period of time and has led to a considerable decrease in the energy input in industrial glass production. The known difficulty that in the course of waste glass collection the consumer does not separate materials precisely concerning the color of the glass and impurities such as ceramics, stones, chinaware, etc. has been overcome in the meantime by reliable automated material separation processes with optoelectronically controlled sorting apparatuses.

For the purpose of color sorting and the recognition of impurities, mostly contactless measuring methods by means of infrared or RGB sensors are used, which initiate a separation of the undesirable impurities from the waste glass material flow or a deflection of colored glasses into fractions provided for this purpose by downstream blow-out or suction nozzles on the basis of the recorded degree of transmission or absorption of light directed against the waste glass material flow. The object of the mixed waste glass material flow to be sorted out is irradiated by radiation sources on a sorting belt or during a free-falling passage, and the radiation passing through the waste glass material flow or reflected therefrom is detected in its intensity by a detection unit and compared with the reference values. An evaluation and control unit which has a data connection with the detecting unit subsequently performs an allocation of the object to a respective fraction and initiates the gripping of the same by pick-ups or a deflection of the same into predetermined containers by means of compressed-air or suction nozzles.

One area of problems that was of only low importance in the recycling of class but which has become more pressing recently is the recognition of special glass in the waste glass material flow. Assortments of glass created for special applications are referred to as special glasses, which in comparison to normal glass (soda-lime glass) have strongly deviating chemical and physical properties, especially a substantially higher melting point and better thermal properties. These include for example glass-ceramics, silica glass, lead glass and temperature-resistant and heat-shock-resistant technical glasses such as borosilicate glass.

The primary production process of special glass is similar to the one in the production of normal glass, but a certain fraction of special oxides is added to the glass melt depending on the respective field of application.

The so-called lead glasses or leaded glass pieces contain lead oxides. Although they are very popular as so-called lead crystal glass as a result of their strong optical refraction and favorable surface working capability, they need to be recycled in special glassworks for environmental and health reasons however, where they are molten again under controlled conditions. On the other hand, lead glass also includes screens (cathode ray tube screens), the components of which comprise a different fraction of lead oxide PbO: the front glass which forms the visible part of the screen has a content of 0.1 to 4% of PbO; in the case of low-lead or lead-free fronts the content is close to <0.1% PbO. The cone glass however has a content of 10 to 25% of PbO. Fractures of screens therefore either belong to the front glass, the cone glass or the transitional region between the front and the cone, which glass pieces thereof are known as front/cone frits and can represent a separate class of glass pieces to be sorted out.

Known methods for sorting special glass work with x-ray sensors, wherein specific chemical components (such as aluminum oxide for example) are excited in the special glass by an x-ray source. As a reaction, the excited elementary particles or electrons will emit energy in form of light, the intensity of which will finally be measured and will be evaluated for the purpose of detection. The industrial market however regards the x-ray sensor method with reservations because the use of x-rays always entails a certain health risk for persons involved around the installation as a result of the extremely short-wave radiation. Moreover, installations that operate according to this method are dimensioned in a relatively large way and are furthermore very expensive.

A further known method for the sorting of special glass operates with the property of fluorescence of special glass. In this case, the glass is irradiated with UV light of a specific wavelength, whereupon it begins to fluoresce in a narrow visible spectral range because the irradiated light will partly be absorbed by impurities contained in the oxidic glass and will be converted into fluorescent radiation. Conclusions can be drawn on the type of the special glass on the basis of the color of the fluorescence. The UV light to be used depends on the type of the special glass to be sorted out. Such a method is known from WO2004/063729A1 for example, with which lead glass can be recognized and sorted out among other things.

It is not possible to detect non-transparent or low-transparent impurities with such a method. Such impurities will be summarized under the term "CSC" (ceramics, stones and chinaware).

SUMMARY OF THE INVENTION

It is therefore an object of the present invention to provide a method and a respective apparatus with which lead glasses can be detected on the one hand and also impurities (ceramics, stones and chinaware) on the other hand.

This object is achieved by a method for detecting leaded glass pieces in a single-layer material flow of objects predominantly consisting of waste glass, with the objects being irradiated with a substantially monochromatic UV light and the fluorescent light resulting therefrom being detected in that the objects are additionally irradiated with visible or infrared light outside of the wavelength range of the fluorescent light;

the transmission light of the visible or infrared light is detected after the passage through the object;

and an object is defined as containing lead if both the fluorescent light for at least one predetermined wavelength range corresponding to the fluorescence of leaded glasses is present in a predetermined intensity range and also transmission light in a predetermined intensity range with intensities of larger zero.

By using visible or infrared light (wavelength 780 nm up to 1 mm), low-transparent or non-transparent impurities (CSC) can be securely identified on the one hand, especially when they emit this fluorescent light in the same spectral range as leaded glass pieces. It can be prevented on the other hand that a piece of glass to which paper adheres and which often also supplies a signal in the wavelength range of the fluorescent light of leaded glass pieces is erroneously identified as lead glass.

Non-leaded glass will therefore have no or only a low intensity in the predetermined wavelength range that is associated with the fluorescent light; the transmission light will have a higher intensity than that of non-transparent or low-transparent impurities.

Leaded glass will have a higher intensity in the predetermined wavelength range which is associated with the fluorescent light than non-leaded glass; the transmission light will have a higher intensity than that of non-transparent or low-transparent impurities.

Non-transparent or low-transparent impurities will have no intensity in the transmission light or only a lower intensity in comparison with transparent glasses with a lead content (but also without a lead content).

Tests have shown that the use of UV-C light which comprises the wavelength range of 100 to 300 nm is very suitable for detecting not only the presence of lead oxides in the glass, but also the content of lead oxides in the glass. It can therefore be provided that the UV light has a wavelength in the range of 100 to 300 nm, especially between 250 and 275 nm, and that the fluorescent light is detected in the wavelength range of 380 to 500 nm.

Especially advantageous embodiments are such that the UV light has a wavelength of approximately 270 nm and the fluorescent light is detected in the wavelength range of 380 to 450 nm, or that the UV light has a wavelength of approximately 254 nm and the fluorescent light is detected in the wavelength range of 420 to 500 nm. The last variant comes with the advantage that conventional UV-C fluorescent tubes with a wavelength of 254 nm can be used; however, the determination of different lead contents is more difficult there than with a UV-C light source with a wavelength of 270 nm.

Since fluorescence is a surface effect, better results are obtained, which means higher intensities of the fluorescent light, if the fluorescent light is measured by means of the incident-light method. This means the UV light source and the detector for fluorescent light are disposed on the same side of the object. Measurement of the fluorescent light by means of the backlighting method also has advantages, with the detector being disposed in this case on the opposite side of the UV light source and measuring the fluorescent light passing through the object and reflected from the edge of the shard, which fluorescent light can be dampened depending on the thickness and coloring of the object. As a result, both the detector for the fluorescent light and the detector for the transmission light can be arranged on one side of the object and they can receive light from approximately the same position of the object.

It is understood that a combination of incident-light and backlight detectors for detecting the fluorescent light is possible.

It is advantageous if as a result of the intensity of the fluorescent light in the predetermined intensity range for leaded glass pieces a further subdivision of the leaded glass pieces is made concerning the lead content. As a result, at least two classes of lead glasses could be filtered out, one with a lower lead oxide content and one with a higher content. This can be applied especially well in the incident-light method, because in this case the intensities are principally higher and are less dependent on the thickness and the color.

As a result, the separation of lead glasses according to different classes of lead content as required by various quality standards could be performed:

Lead-free and low-lead glass (<0.1% PbO)
Lead glass A (0.1 to approx. 5% PbO)
Lead glass B (>approx. 5% PbO)

The use of visible light or infrared light also allows to process by means of image processing the image recorded by means of a detector, mostly a COD camera, and to thereby also approximately recognize the shape of an object. This also allows determining a partial area such as the boundary area or the inside area (=area within the boundary area) for each examined object as a result of radiation with visible or infrared light, and only the intensity of the fluorescent light of the partial area is used for defining the lead content. Tests have shown that the intensity of the fluorescent light is higher at the fracture edges of the glass pieces than within the boundary areas. As a result, the intensities can be compared better in the boundary areas between different pieces of glass for example.

It can be provided as also performed in already known methods that an object defined as leaded and/or as an impurity is removed from the material flow by blow-out nozzles by means of compressed air for example.

An object will be defined as an impurity if its transmission light lies in an intensity range which lies beneath the intensity range for leaded glass pieces.

It can also be provided that the light from the UV light source is deflected and filtered by at least one mirror filter.

The apparatus for performing the method in accordance with the invention is characterized in that it comprises at least:

a substantially monochromatic UV light source, with which a single-layer material flow of objects of predominantly waste glass can be illuminated;

a first detector for detecting the fluorescent light generated by the UV light source in the object;

a second light source which is capable of emitting light in the visible range or infrared light outside of the wavelength range of the fluorescent light;

a second detector for detecting the transmission light of the visible or infrared light after passing through the object;

a device for producing a single-layer material flow of waste glass, with which the material flow can be guided past the UV light source and the second light source;

and a device for sorting out leaded glass pieces, which will sort out an object when both fluorescent light is present in a predetermined intensity range for at least one predetermined wavelength range corresponding to the fluorescence of leaded glasses and also transmission light in a predetermined intensity range with an intensity of larger zero.

As already explained in connection with the method in accordance with the invention, the UV light source can emit UV light with a wavelength in the range of 100 to 300 nm, especially between 250 and 275 nm, and the first detector can detect fluorescent light only in the wavelength range of 380 to 500 nm. Preferred embodiments are UV light sources with a wavelength of approximately 270 nm and detectors for fluorescent light in the wavelength range of 380 to 450 nm on the one hand and UV light sources with a wavelength of approximately 254 nm and detectors for fluorescent light in the wavelength range 420 to 500 nm on the other hand.

In order to perform the backlighting method it can be provided that the UV light source and the first detector are disposed on different sides of the material flow.

In order to arrange the apparatus in accordance with the invention as compact as possible, it can be provided that the UV light source and the second light source are disposed in a common housing and/or the first and second detector are disposed in a common housing.

In order to enable the elimination of undesirable wavelengths, especially such of visible light, from the spectrum of the UV light source, the UV light should be filtered. It can be provided for this purpose that the UV light source is built into a housing with at least one mirror filter in such a way that the light from the UV light source is deflected and filtered via at least one mirror filter, and is especially deflected by 180° by two mirror filters arranged normally with respect to each other.

A housing for a UV light source for use in a method in accordance with the invention is also claimed, with the UV light source being installable into the housing with at least one mirror filter in such a way that the light from the UV light source is deflected and filtered via at least one mirror, and is especially deflected by 180° by two mirror filters arranged normally with respect to each other.

The invention will be explained in closer detail by reference to the schematic drawings which represent an embodiment of an apparatus in accordance with the invention. The backlighting method is used in both cases, which means the UV light source and the detector for fluorescent radiation are disposed on different sides of the waste glass material flow.

DETAILED DESCRIPTION OF THE PREFERRED EMBODIMENT

Figure 1:
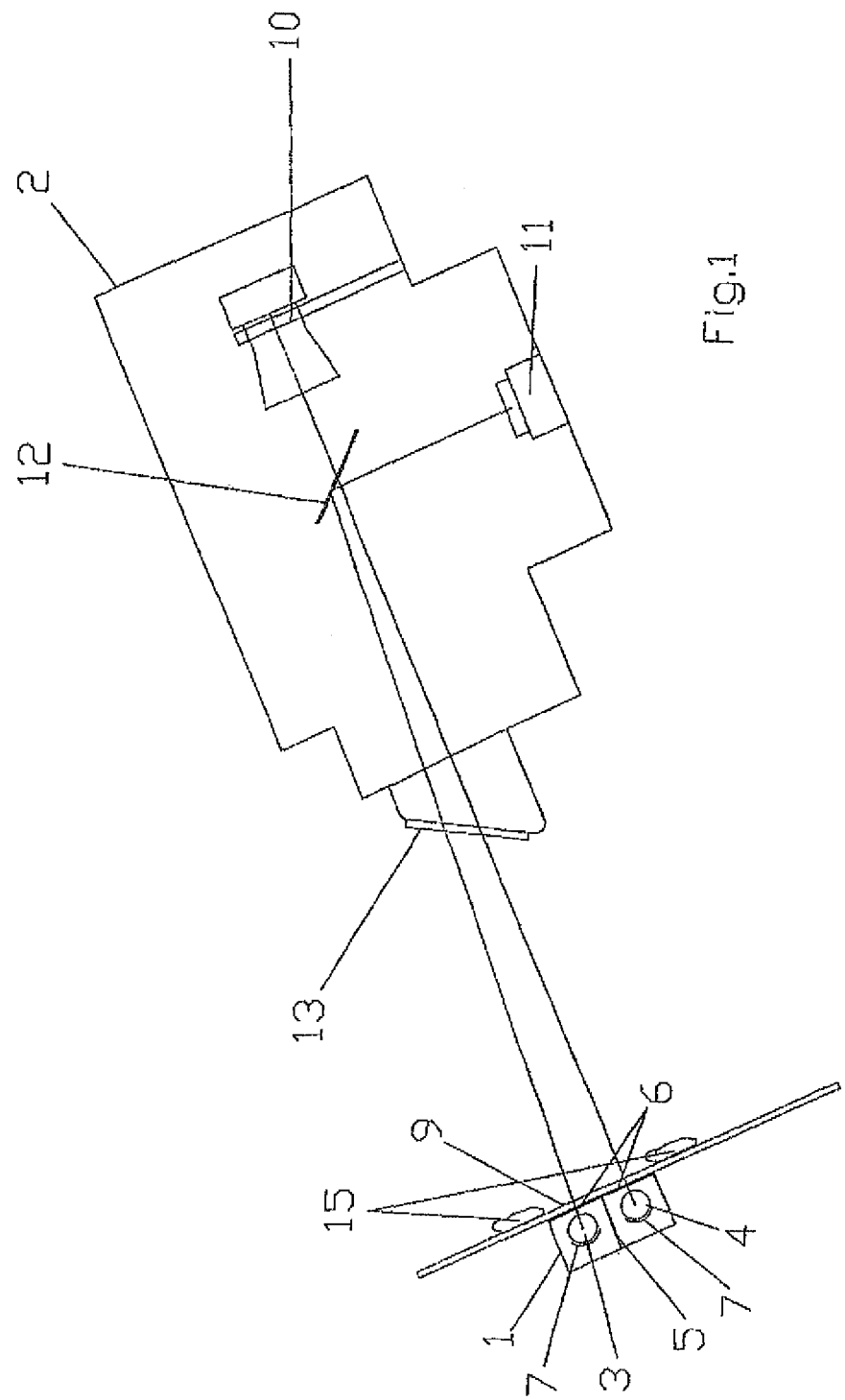
FIG. 1 shows an apparatus in accordance with the invention with filters for the UV light source.

In FIG. 1, both a UV light source 3 and a second light source 4 are installed in a housing 1 for light sources, The UV light source 3 can emit UV light in the range of 100 to 280 nm, especially between 250 and 275 nm. It can be arranged in form of a UV-C lamp, which is also known as a UV-C fluorescent lamp or UV-C fluorescent tube. One or several UV-C LEDs (LED line) can also be used instead of a UV tube.

The second light source 4 can emit light in the visible range (wavelength of 380 to 780 nm) and/or in the infrared range (wavelength of 780 nm to 1 mm) and can be arranged (as in this example) as a fluorescent lamp (VIS lamp) with wavelengths in the visible range. It is also possible to use one or several color or infrared LEDs (LED line) instead of a lamp (VIS lamp).

LEDs offer several advantages over fluorescent tubes:
Better controllability of intensity
Higher intensity
Many different and also narrow wavelength ranges are possible
Width of illumination (LED line) and illuminated area can be chosen freely by the arrangement of several LEDs
Predetermination of an intensity profile is possible The disadvantages at least of LEDs in the UV-C range are the currently higher purchase costs and the higher diffusion effort in comparison with fluorescent tubes.

The two light sources 3, 4 are separated from one another by an opaque separating wall 5.

In the present example in FIG. 1, a UV-C lamp 3 emits UV-C radiation with a maximum intensity at a wavelength of 254 nm and is installed in the housing 1 in such a way that the UV light is guided by a reflector 7 disposed behind the UV-C lamp 3 in the direction towards the detectors. The UV light further passes through a filter 6 which absorbs the major part of the light in the visible range emitted by the UV-C lamp 3 and therefore hardly conducts any visible light in the wavelength range of the fluorescent light to the detectors. If blue light for example would reach the detector for fluorescent light from the UV-C lamp 3, it would detect this light as fluorescent light radiation because it also lies in the range of the blue light.

The VIS light emitted by the second light source also passes through a filter 6, which absorbs the emitted light in the UV and fluorescent range (<500 nm).

The housing 1 consists of a silica-glass pane 9 at least in the region of the UV light passage. Silica glass has a high optical transparency for UV-C light. The silica-glass pane 9 can also cover the light passage of the visible light.

The silica-glass pane 9 is also used as a chute for the objects 15 (glass shards, impurities) to be examined. In the mounted state of the apparatus in accordance with the invention, it has an inclination of approximately 25° in relation to the perpendicular. The objects 15 will slide downwardly on said chute and are illuminated in this process by the two light sources 3, 4.

The distance between the fluorescent light to be detected and the transmission light to be detected (from light source 4) should ideally be as low as possible (and ideally congruent), so that both detectors—the one for the fluorescent light and the one for the transmission light—are able to map an image of the moved objects 15 as congruently as possible. The distance between the central axes of the light rays of the visible light and the UV light is approximately 50 mm in this example when they exit from housing 1.

Both the visible light of the VIS lamp 4 which is allowed to pass through the objects and also the fluorescent radiation in the blue visible range which is optionally induced by the UV light pass through a protective glass 13 into the further housing 2, where a detector 11 is attached for detecting the fluorescent light on the one hand and where a detector for detecting the transmission light of the second light source 4 is also arranged on the other hand.

The protective glass 13 consists of normal glass and protects the interior of housing 2 from dust and UV-C radiation.

The detector 11 for detecting the fluorescent light is sensitive in a wavelength range of 400 to 1000 nm. The sensitivity can further be changed by filters, e.g. to the relevant wavelength range of 420 to 500 nm in this case for example. (If UV light with a wavelength of approximately 270 nm were used, the filter would be set in such a way that only fluorescent light in the wavelength range of 400 to 450 nm can be detected). The detector 11 will usually be arranged as a camera. It can be arranged as a so-called TDI camera 11 for example.

In order to prevent a disturbance of the fluorescent light by a further light source in this wavelength range, the second light source 4 should potentially only emit light outside of this frequency range. It is frequently the case in practice however that even light sources in the yellow or red range, which therefore "emit light in the visible range or infrared light outside of the wavelength range of fluorescent light" as defined, still have a blue fraction in the light which might optionally have to be filtered out, as explained above in connection with filter 6 for the second light source 4.

It has been noticed that especially for distinguishing green and brown glass from CSC visible light in the range of yellow/orange (approximately 590 nm) provides the best results.

In order to detect the transmission light from the second light source 4 it is principally sufficient when a detector 10 such as a camera for example can supply at least one image of glass pieces in grey shadings. The position and the shape of the object 15 which is necessary in order to optionally remove the object from the flow of material by means of downstream removal devices can then be determined on the one hand. On the other hand, the optical transparency of the object (piece of glass) 15 is thereby determined and it has been recognized as being transparent (whereby it can still be leaded or non-leaded) or as low-transparent or non-transparent (in which case it would be an impurity). Accordingly, the impurity will then be removed from the flow of material by the removal devices. The edges and the inside areas of the pieces of glass can also be defined by means of this detector by image recognition and the intensity of the fluorescent radiation can be used for evaluating the lead glass content on the basis of only these partial areas of the shard of glass.

The detector 10, which is usually a camera, is therefore at least sensitive in the wavelength range in which the second light source 4 emits light. A so-called RGB camera 10 is used in this example. An RGB signal is processed in the same, i.e. the colors red, green and blue are respectively transmitted and stored in a separate channel.

A highly sensitive detector is principally necessary for detecting the fluorescent light, which is usually a camera. In this embodiment, a so-called TDI camera 11 was used. It contains a CCD sensor like the RGB camera. However, it contains TDI (Time Delay Integration) elements which are especially sensitive and still supply good recordings of moved objects.

Both fluorescent light and also transmitted light impinge on a beam splitter 12 which reflects blue light in the wave length range of 400 to 500 nm for example as completely as possible and allows visible light >500 nm (transmitted light) to pass through as completely as possible. The reflected light beam is guided into the TDI camera 11; the light beam that is allowed to pass through reaches the RGB camera 10.

The detected data are supplied to an evaluation and control unit which allocates the individual glass shards to the different fractions of
  lead glass (optionally with different fractions with different lead content);
  impurities (ceramics, stones and chinaware, "CSC");
  normal glass, and
  optionally glass ceramic materials;
and controls the removal units which move the pieces of glass to the respective containers.

Figure 2:
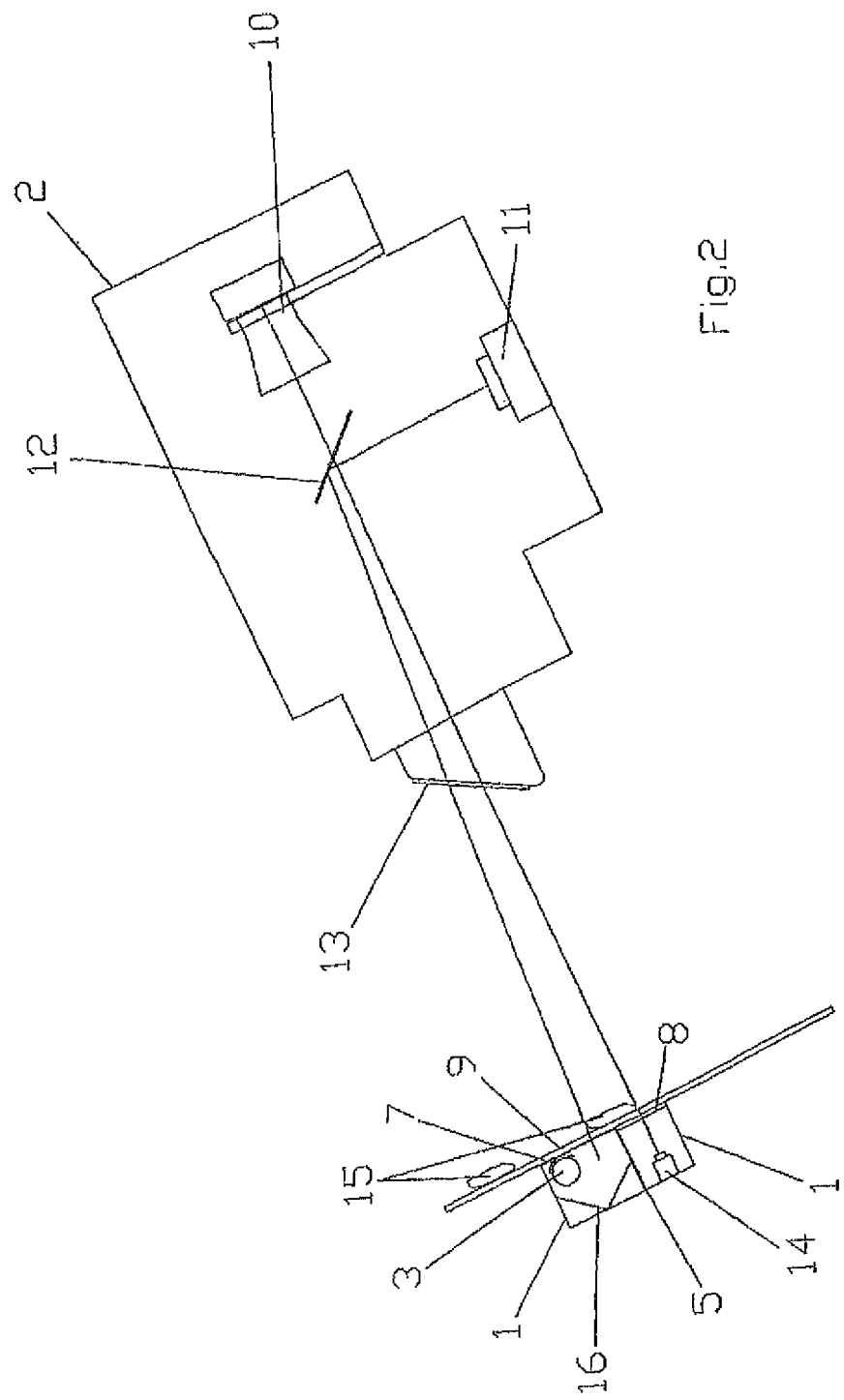
FIG. 2 shows an apparatus in accordance with the invention with mirror filters for the UV light source.

In FIG. 2, both a UV light source 3 and a second light source 14 are installed in a housing 1 for light sources, but are separated from one another by an opaque separating wall 5.

The UV light source 3 can emit UV light in the range of 100 to 280 nm, especially between 250 and 275 nm. It is arranged in this case again in form of a UV-C lamp. It would also be possible to use one or several UV-C LEDs instead of a UV tube.

The second light source 14 can emit light in the visible range (wavelength of 380 780 nm) and/or in the infrared range (wavelength of 780 nm to 1 mm) and can be arranged as in this example as one or several infrared LEDs (LED line). Similarly, a lamp with wavelengths in the visible range and/or in the infrared range or one or several daylight or color LEDs (LED line) could also be used.

The UV-C lamp 3 emits UV-C radiation with a wavelength of 254 nm and is installed in the housing 1 in such a way that the UV light is guided away from the detectors by a reflector 7 arranged in the direction of the detectors and deflected by 180° by two mirror filters 16 which are arranged at a right angle with respect to each other and is therefore guided in the direction towards the detectors. The mirror filters 16 are mirrors which are provided with a coating which absorbs the major part of the light in the visible range which is emitted by the UV-C lamp 3 and therefore virtually does not reflect any visible light in the wavelength range of the fluorescent light and guides it to the detectors. If blue light would reach the detector for fluorescent light from the UV-C lamp 3 for example, it would be detected as fluorescent radiation because it also lies in the range of the blue light. Instead of coated mirror filters 16 or in addition thereto, it is also possible to provide filters for visible light in the wavelength range of the fluorescent light in the beam path of the UV light.

Mirror filters 16 come with the advantage that they can be produced at low cost even in large widths of approximately 1000 mm for example, which corresponds to the width of the conveyor belts or the chute for waste glass. Classical filters come with disadvantage on the one hand that they can only be produced in small widths (<200 mm) and therefore no integral filter can be produced for the apparatus in accordance with the invention which is able to cover the entire width of the conveyor belt or the chute for the waste glass.

A mirror filter 16 has a height of approximately 5 to 10 cm in this example (as measured in the plane of projection), especially 7 cm in this case. The width (as measured normally to the plane of projection) is 50 to 150 cm, especially 100 cm in this case.

A sheet metal of a thickness of 1 to 2 mm is used as the base material for the mirror filter 16. The coating consists of oxides and has a thickness of a few micrometers.

The infrared light of the infrared LEDs 14 is guided through a diffusion screen 8 in order to make the light of the point-shaped infrared LEDs 14 more homogeneous and leaves the housing 1 parallel to the UV light. It is also possible to use other devices instead of a diffusion screen 8 in order to distribute the light more evenly, e.g. a reflection conduit which is mirrored on its inside, as is illustrated in AT 10184 U1.

The housing 1 consists of a silica glass pane 9 at least in the region of the UV light passage, as shown in FIG. 1. The silica glass pane 9 can also cover the light passage of the second light source (the infrared LEDs 14) and can be used as a chute for the objects to be examined.

The distance between the fluorescent light to be detected and the transmission light to be detected should also be as small as possible (and ideally congruent), so that both detectors (the one for the fluorescent light and the one for the transmission light) are able to project the image of the moved object in the highest congruent manner. The distance between the central axes of the light beams of the infrared light and the UV light is in this case also approximately 50 mm when they exit from the housing 1.

Both the infrared light of the infrared LEDs 14 which is allowed to pass through the objects 15 and also the fluorescent radiation in the blue visible range which is optionally induced by the UV light will pass through a protective glass 13, as described under FIG. 1, into the further housing 2, where a detector 11 for detecting the fluorescent light is attached on the one hand, which detector is to be arranged as described under FIG. 1 and which is arranged in this case too in FIG. 2 as a so-called TDI camera 11, and where on the other hand a detector 10 for detecting the transmission light of the second light source 14 (the infrared LEDs 14) is arranged. The detector 10, which is usually a camera again, is therefore sensitive in at least the wavelength range in which the second light source 14 emits light, i.e. in this case in a range within the wavelength range of 780 nm to 1 mm. In this case too, an RGB camera with an optionally provided upstream filter can also be used here.

In order to prevent any disturbance in the detection of the fluorescent light by a further light source in this wavelength range, the second light source should only emit light outside of this frequency range. A light was therefore chosen for this embodiment which is as far as possible away from the fluorescent light, namely infrared light with a wavelength of 860 nm.

It is also possible to use visible light from LEDs in the range of yellow/orange (approximately 590 nm) especially for distinguishing green and brown glass from CSC, which ensures the best results for this purpose.

As already explained in connection with FIG. 1, it is principally sufficient for detecting the transmission light that the detector 10 such as a camera for example is capable of supplying at least one image of objects 15 in grey shading. The shape and position of the object 15 can then be determined therefrom, which is necessary in order to optionally remove the object 15 by means of downstream removal devices from the material flow. On the other hand, the optical transparency of the object (piece of glass) 15 is determined thereby and it is recognized as transparent (it can still be leaded or non-leaded) or as low-transparent or non-transparent (in which case it would be an impurity). The impurity will then accordingly be removed by the removal devices from the material flow. This detector can also be used for defining the edges and inner regions of the pieces of glass by image recognition and the intensity of the fluorescent radiation can be used only in these partial areas of the glass shard for evaluating the lead glass content.

Both fluorescent light and also transmitted infrared light will impinge on a beam splitter 12 which reflects blue light in the wavelength range of 400 to 500 nm for example as completely as possible and which allows infrared light such as in the wavelength range of 860 nm to pass through to the highest possible extent. The reflected light beam is guided to the TDI camera 11, and the light beam that is allowed to pass through is guided to the RGB camera 10. The detected data are supplied to an evaluation and control unit which associates the individual pieces of glass to the different fractions of lead glass (optionally with different fractions with different lead content);
impurities (ceramics, stones and chinaware, "CSC");
normal glass, and
optionally glass ceramic materials;

and controls the removal units which move the pieces of glass to the respective containers.

LIST OF REFERENCE NUMERALS

1 Housing for Light Sources
2 Housing for Detectors
3 UV Light Source (UV-C lamp)
4 Second Light Source (VIS lamp)
5 Separating Wall
6 Filter
7 Reflector
8 Diffusion Screen
9 Silica Glass Pane
10 Detector for Detecting the Transmission Light (RGB camera)
11 Detector for Detecting the Fluorescent Light (TDI camera)
12 Beam Splitter
13 Protective Glass
14 Second Light Source
15 Object (piece of glass or impurity)
16 Mirror Filter

The invention claimed is:

1. A method for detecting leaded pieces of glass in a single-layer material flow of objects made predominantly of waste glass, the method comprising steps of:
a first light source irradiates the objects with substantially monochromatic UV light;
a first detector detects fluorescent light resulting from the irradiation of the objects with the substantially monochromatic UV light;
a second light source irradiates the objects with visible or infrared light outside of the wavelength range of the fluorescent light;
a second detector detects transmission light of the visible or infrared light after the passage through the objects;
an evaluation and control unit receives detection data from the first detector and from the second detector and determines from the detection data if an object of the objects contains lead, the object being defined as containing lead if both the fluorescent light for at least one predetermined wavelength range corresponding to the fluorescence of leaded glasses is present in a predetermined intensity range and also transmission light in a predetermined intensity range with an intensity of larger zero; and
if the evaluation and control unit determines that the object contains lead, the object is removed from the material flow.

2. The method according to claim 1, wherein the UV light has a wavelength in the range of 100 to 300 nm and the fluorescent light is detected in the wavelength range of 380 to 500 nm.

3. The method according to claim 2, wherein the UV light has a wavelength of approx. 270 nm and the fluorescent light is detected in the wavelength range of 380 to 450 nm.

4. The method according to claim 2, wherein the UV light has a wavelength of approx. 254 nm and the fluorescent light is detected in the wavelength range of 420 to 500 nm.

5. The method according to claim 1, wherein the fluorescent light is measured by the backlighting method.

6. The method according to claim 1, wherein a further subdivision of the leaded pieces of glass is made with respect to the lead content as a result of the intensity of the fluorescent light in the predetermined intensity range.

7. The method according to claim 1, wherein a partial area such as the boundary area or the inner area of the object is determined for each examined object on the basis of radiation with visible or infrared light and only the intensity of the fluorescent light of the partial area will be used for defining the lead content.

8. The method according to claim 1, wherein the evaluation and control unit determines if the object has a low-transparent or non-transparent impurity, the object being defined as a low-transparent or non-transparent impurity when its transmission light lies in an intensity range which lies beneath the intensity range for leaded pieces of glass.

9. The method according to claim 8, wherein if the evaluation and control unit determines that the object has a low-transparent or non-transparent impurity, the object is removed from the material flow.

10. The method according to claim 1, wherein the light from the UV light source is deflected and filtered via at least one mirror filter.

11. An apparatus comprising:
a substantially monochromatic UV light source, with which a single-layer material flow of objects of predominantly waste glass can be illuminated;
a first detector for detecting the fluorescent light generated by the UV light source in the object;
a second light source which is capable of emitting light in the visible range or infrared light outside of the wavelength range of the fluorescent light;
a second detector for detecting the transmission light of the visible or infrared light after passing through the object;
a device for producing a single-layer material flow of waste glass, with which the material flow can be guided past the UV light source and the second light source; and
a device for sorting out leaded glass pieces, which will sort out an object when both fluorescent light is present in a predetermined intensity range for at least one predetermined wavelength range corresponding to the fluorescence of leaded glasses and when transmission light in a predetermined intensity range with an intensity of larger zero is also present, the device comprising an evaluation and control unit receiving detection data from the first detector and from the second detector and programmed to determine from the detection data if the object should be sorted out.

12. The apparatus according to claim 11, wherein the UV light source is capable of emitting UV light with a wavelength in the range of 100 to 300 nm and the first detector is capable of detecting fluorescent light only in the wavelength range of 380 to 500 nm.

13. The apparatus according to claim 12, wherein the UV light has a wavelength of approx. 270 nm and the fluorescent light is detected in the wavelength range of 380 to 450 nm.

14. The apparatus according to claim 12, wherein the UV light has a wavelength of approx. 254 nm and the fluorescent light is detected in the wavelength range of 420 to 500 nm.

15. The apparatus according to claim 11, wherein the UV light source and the first detector are disposed on different sides of the material flow.

16. The apparatus according to claim 11, wherein the UV light source and the second light source are disposed in a common housing.

17. The apparatus according to claim 11, wherein the first and second detector are disposed in a common housing.

18. The apparatus according to claim 11, wherein the UV light source is installed in a housing with a first mirror filter and a second mirror filter disposed normally with respect to the first mirror filter in such a way that the light from the UV light source is deflected by 180° and filtered via the first and second mirror filters.

* * * * *